(12) United States Patent
Meeker et al.

(10) Patent No.: US 12,053,557 B2
(45) Date of Patent: Aug. 6, 2024

(54) APPARATUS FOR CLEANING PROSTHETIC LINER AND ASSOCIATED METHODS

(71) Applicant: Douglas Meeker, Port Orange, FL (US)

(72) Inventors: Douglas Meeker, Port Orange, FL (US); Wolfgang Streer, Orlando, FL (US)

(73) Assignee: Douglas Meeker, Port Orange, FL (US)

( * ) Notice: Subject to any disclaimer, the term of this patent is extended or adjusted under 35 U.S.C. 154(b) by 525 days.

(21) Appl. No.: 17/249,746

(22) Filed: Mar. 11, 2021

(65) Prior Publication Data

US 2021/0283291 A1    Sep. 16, 2021

Related U.S. Application Data

(60) Provisional application No. 62/987,900, filed on Mar. 11, 2020.

(51) Int. Cl.
    *A61L 2/18*         (2006.01)
    *A61L 2/26*         (2006.01)

(52) U.S. Cl.
    CPC    *A61L 2/18* (2013.01); *A61L 2/26* (2013.01); *A61L 2202/14* (2013.01); *A61L 2202/17* (2013.01); *A61L 2202/21* (2013.01)

(58) Field of Classification Search
    CPC .......... A61L 2/18; A61L 2/26; A61L 2202/17; A61L 2202/21
    See application file for complete search history.

(56) References Cited

U.S. PATENT DOCUMENTS

| | | | |
|---|---|---|---|
| 9,140,497 B2 * | 9/2015 | Al-Shahrani | F26B 25/18 |
| 2012/0084994 A1 * | 4/2012 | Alston | D06F 58/203 34/90 |
| 2017/0045295 A1 * | 2/2017 | Durham | A47B 45/00 |

FOREIGN PATENT DOCUMENTS

| | | | | |
|---|---|---|---|---|
| EP | 1980273 A1 * | 10/2008 | | A61L 2/07 |
| WO | WO-2020183407 A1 * | 9/2020 | | A61B 90/70 |

* cited by examiner

*Primary Examiner* — Sean E Conley
*Assistant Examiner* — Justin Hwang
(74) *Attorney, Agent, or Firm* — Daniel C. Pierron; Widerman Malek, PL (57) ABSTRACT

A prosthetic liner cleaning apparatus including a base that permits a first fluid to flow therethrough, includes an input aperture, a center member comprising an output aperture, and a duct in fluidic communication with each of the input aperture and the output aperture. The apparatus further includes a dispenser positioned in fluidic communication with the duct and configured to dispense a second fluid into the flow of the first fluid in the duct and a stem including a lower end, an upper end, and a fluid channel positioned in fluidic communication with each of the lower end and the upper end, the stem being attached to the base at the lower end and extending upward therefrom, and the fluid channel positioned in fluidic communication with the output aperture. The apparatus further includes a cap member attached to the stem at the upper end thereof to eject fluid.

15 Claims, 4 Drawing Sheets

APPARATUS FOR CLEANING PROSTHETIC LINER AND ASSOCIATED METHODS

FIELD OF THE INVENTION

The present invention relates to an apparatus for cleaning a prosthetic liner and methods for cleaning prosthetic liners.

BACKGROUND OF THE INVENTION

Prosthetic devices are known to cause irritation and potential injury when attached directly to the body of the wearers. For this reason, liners positioned between the wearer and the prosthetic device are employed. Such liners are desirously tight against the skin of the wearer and, in order to maximize usefulness of the prosthetic device and prevent slippage between the device and the wearer, liners are often made of materials with relatively high coefficients of static friction. Materials having such a property tend to be non-porous. As a result when the wearer sweats at the location covered by the liner, bacteria can form that can be malodorous and potentially cause an infection. Accordingly, prosthetic liners need to be cleaned regularly and frequently to remove such bacteria.

In order to provide sufficient surface area to facilitate attachment of the prosthetic device to the wearer, liners need to cover the entire area of the wearer that the prosthetic device would normally attach. This results in the liners tending to have sleeve-like configuration, having an opening at one end, a cylindrical length that can be circular, ellipsoid, or any other shape, and a closed end opposite the open end. The wearer may slide the open end over their body until the closed end abuts their body. As a result of this configuration, prosthetic liners can be difficult to clean. Holding them upright, i.e. with the open end facing upwards, results in cleaning and rinsing solutions collecting in the liner, reducing the ability to rinse off bacteria and potentially stretching the liner from the weight of the collected solution. To avoid this, the liner needs to be oriented such that the open end faces downward. This makes cleaning more difficult, as standard faucets direct fluid downward. Moreover, the use of hoses that can be manually positioned so that they eject fluid upward requires the user to commit one of their hands to holding the hose, constraining their ability to effectively clean the liner, giving rise to the potential of inadequate cleaning and subsequent bacterial growth. Alternatively, if the user of the device is missing an arm and/or hand, they may physically unable of simultaneously manipulating a hose and the liner at the same time. Accordingly, there is a need in the art for a cleaning device that is structured to facilitate the cleaning of prosthetic liners that requires the use of only one hand at a time.

SUMMARY OF THE INVENTION

An embodiment of the invention is directed to a prosthetic liner cleaning apparatus comprising a base configured to permit a first fluid to flow therethrough, the base comprising an input aperture, a center member comprising an output aperture, and a duct in fluidic communication with each of the input aperture and the output aperture, the duct being configured to permit the first fluid to flow therethrough. The apparatus further comprises a dispenser positioned in fluidic communication with the duct and configured to dispense a second fluid into the flow of the first fluid in the duct, a stem comprising a lower end, an upper end, and a fluid channel positioned in fluidic communication with each of the lower end and the upper end, the stem being attached to the base at the lower end and extending upward therefrom, and the fluid channel positioned in fluidic communication with the output aperture, and a cap member attached to the stem at the upper end thereof. The cap member comprises an entry aperture positioned in fluidic communication with the fluid channel, an exit aperture, and a distributor configured to redirect the flow of fluid from the entry aperture in the direction of the exit aperture.

In some embodiments, the base may further comprise a plurality of legs, each leg extending radially outward from the center member. A leg of the plurality of legs may comprise the input aperture and at least a portion of the duct, such that the duct extends from the input aperture comprised by the leg to the output aperture comprised by the center member. Furthermore, the leg comprising the input aperture may further comprise a concavity positioned intermediate the input aperture and the duct, the concavity configured to permit tubing to be positioned there within such that the tubing passes through the input aperture, through the concavity, and be positioned in fluidic communication with the duct. Additionally, the duct may comprise threads configured to engage with cooperating threads of the tubing to establish fluidic communication there between.

In some embodiments, the apparatus may further comprise a pressure modifying device configured to temporarily decrease the pressure of the first fluid as it flows through the base. The dispenser may be positioned to dispense the second fluid into the flow of the first fluid while the pressure of the first fluid is decreased. The pressure modifying device may be a venturi tube.

In some embodiments, the dispenser may comprise a reservoir configured to retain the second fluid prior to being dispensed and a dispensing channel positioned in fluidic communication with each of the reservoir and the duct configured to permit the second fluid to flow from the reservoir and be dispensed into the flow of the first fluid. In some further embodiments, the dispenser may further comprise a flow control member configured to control a flow rate of the second fluid through the dispensing channel. In some embodiments, the dispenser may further comprise a primer configured to at least one of drat the second fluid from the reservoir and initiate a flow of the second fluid from the reservoir.

In some embodiments the exit aperture may be a first exit aperture, the cap member may further comprise a second exit aperture, and the distributor may be configured to redirect the flow of fluid towards each of the first exit aperture and the second exit aperture. In some further embodiments, the first exit aperture may be configured to disperse fluid into a hemisphere generally above the cap member, and the second exit aperture may be configured to disperse water annularly radially outward from the cap member. Additionally, the cap member may further comprise a flange extending radially outward from the cap member and configured to offset a liner placed thereupon from the cap member.

In some embodiments, the stem may further comprise a plurality of holes in fluidic communication with the fluid channel such that fluid flowing through the fluid channel is expulsed through the plurality of holes.

Further embodiments of the invention may be directed to a method of cleaning a prosthetic liner using a washing apparatus comprising a cleaning agent apparatus, an expulsion portion, and a stem portion, the method comprising placing the liner over the stem portion of the washing apparatus, causing a flow of a first fluid to enter the washing apparatus, operating the cleaning agent apparatus to cause a flow of a second fluid to enter the flow of the first fluid, such that a mixture of the first and second fluids is created, vertically translating the liner up and down to coat an inner surface of the liner with the fluid mixture expulsed from the expulsion portion, operating the cleaning agent apparatus to cease the flow of the second fluid into the flow of the first fluid, and permitting the flow of only the first fluid to be expulsed onto the inner surface of the liner.

In some embodiments, the method may further comprise causing cessation of the flow of the first fluid. In some embodiments, the method may further comprise resting the liner on an upper portion of the washing apparatus while permitting the flow of only the first fluid to be expulsed onto the inner surface of the liner.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides an apparatus for the cleaning of prosthetic liners. Prosthetic liners may be understood as material that is positioned between a prosthesis and the body of the user. The use of prosthetic liners may reduce complications from prosthesis use including interface site irritation and infection.

Referring now to FIGS. 1-4, a cleaning apparatus 100 according to an embodiment of the invention is presented. The cleaning apparatus 100 may comprise a base 110, a stem 120, an upper cap member 130, and a dispenser 140. The base 110 may be configured to interface with the ground in an environment within which the cleaning apparatus 100 may be operated. In some embodiments, the base 110 may comprise a plurality of legs 112 extending radially outward and from a center member 114 of the base 110 to provide multilateral stability, preventing the cleaning apparatus 100 from tipping over. In the present embodiment, the base 110 comprises three legs 112', 112", 112''' extending outward from the center member 114 to form a wye shape. While the current embodiment includes three legs, any number of legs is contemplated and included within the scope of the invention. In some embodiments, the plurality of legs 112 may be generally hollow, having an outer wall 115. In some embodiments, the plurality of legs 112 may comprise an opening on a lower portion thereof, defining a concavity 117 there within.

Figure 1:
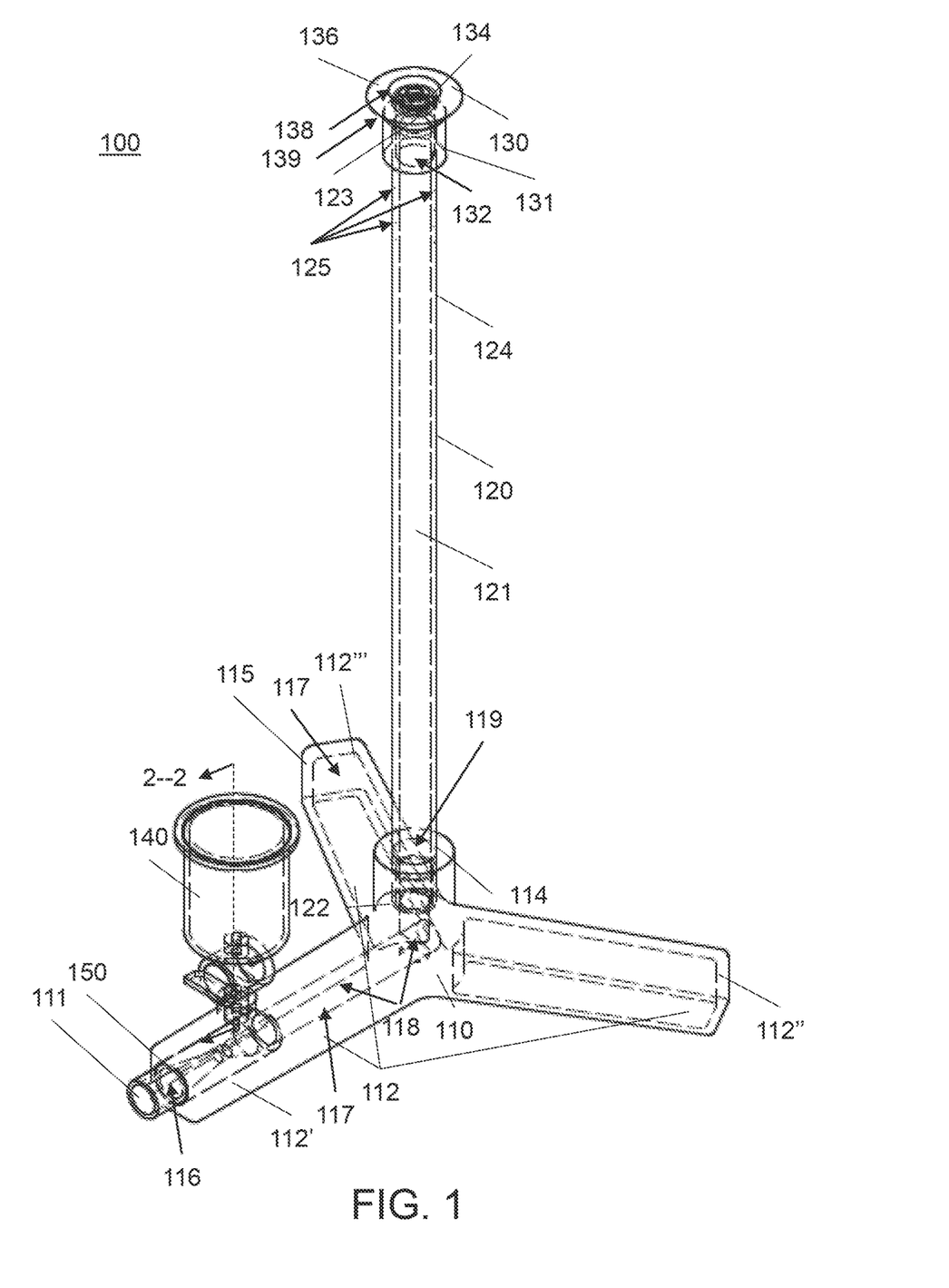
FIG. 1 is a perspective view of a prosthetic liner cleaning apparatus according to an embodiment of the invention.

In some embodiments, the cleaning apparatus 100 may have a height within a range from 10 inches to 40 inches. In some embodiments, the cleaning apparatus 100 may have a height within a range from 15 inches to 30 inches. In some embodiments, the cleaning apparatus 100 may have a height within a range from 17.5 inches to 25 inches. In some embodiments, the cleaning apparatus 100 may have a height within a range from 19 inches to 20 inches.

The width of the cleaning apparatus may be defined by a widest dimension of the base 110. In some embodiments, the cleaning apparatus 100 may have a width within a range from 5 inches to 25 inches. In some embodiments, the cleaning apparatus 100 may have a width within a range from 7.5 inches to 15 inches. In some embodiments, the cleaning apparatus 100 may have a width within a range from 9 inches to 13 inches. In some embodiments, the cleaning apparatus 100 may have a width within a range from 11 inches to 12 inches.

The base 110 may further be configured to facilitate the flow of fluid from external the cleaning apparatus 100, through the base 110, and into the stem 120 to enable cleaning of a prosthetic liner positioned on the cleaning apparatus. In the present embodiment, leg 112' and center member 114 are configured to permit fluid to flow therethrough. Moreover, leg 112' may comprise an input aperture 116 at an end that is opposite the center member 114. The input aperture 116 may be configured to permit tubing to pass therethrough into the concavity 117. In the present embodiment, an input member 111 may be positioned within the input aperture 116 and be configured to be positioned in fluidic communication with a fluid source. For example, the input member 111 may be configured to couple to a hose that is connected to a faucet, spigot, fluid pump, or other fluid source that may cause a first fluid to flow into the input member 111.

Additionally, the base 110 may comprise a duct 118 and an upper aperture/exit aperture 119. The upper aperture 119 may be defined in an upper portion of the center member 114. The duct 118 may be configured to extend through leg 112' and the upper aperture 119. Moreover, the upper aperture 119 may be configured to permit at least a portion of the stem 120 to be positioned there within, facilitating attachment of the base 110 and the stem 120. The attachment between the stem 120 and the base 110 may position the duct 118 in fluid communication with a fluid conduit of the stem 120. Any means or methods of attachment as is known in the art may used to attach the base 110 and the stem 120, including, but not limited to, interference fit, threaded engagement, and the like. Accordingly, in some embodiment, the duct 118 may comprise threads adjacent to the upper aperture 119 to facilitate attachment of the stem 120 thereto. In some embodiments, the attachment may be reversible, such that the base 110 and the stem 120 may be detached to deconstruct the cleaning apparatus 100 when not in use. Such removable attachment may facilitate the storage of the cleaning apparatus 100 between uses.

In some embodiments, the duct 118 may be defined as a cavity within the base 110, specifically within leg 112' and center member 114. In some embodiments, the duct 118 may be tubing positioned within leg 112' and center member 114. It is contemplated and included within the scope of the invention that all means and methods of creating a channel for enabling fluidic flow from the input aperture 116 to the upper aperture 119 are contemplated and included within the scope of the invention.

In some embodiments, the base 110 may have a height within a range from 1 inch to 3 inches. In some embodiments, the base 110 may have a height within a range from 1.5 inches to 2.5 inches. In the present embodiment, the base 110 has a height of approximately 2 inches.

Figure 2:
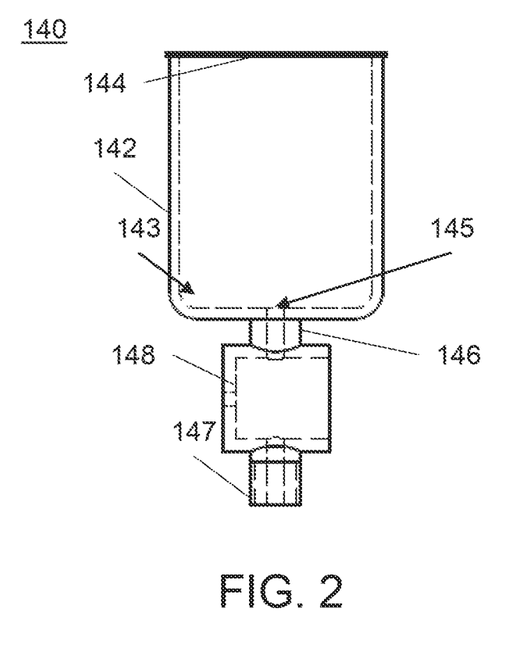
FIG. 2 is a side sectional view of a dispenser of the prosthetic liner cleaning apparatus of FIG. 1 taken through line 2-2.

The cleaning apparatus 100 may further comprise a pressure modifying device. Such a device may modify the pressure of fluid flowing through the cleaning apparatus 100. In the present embodiment, the cleaning apparatus 100 comprises a venturi tube 150 positioned within the concavity 117 of leg 112' and in fluidic communication with the input member 111. The venturi tube 150 may be configured to decrease the pressure of a first fluid flowing therethrough to facilitate the addition of a second fluid from the dispenser 140. Use of the venturi tube 150 to temporarily decrease the pressure of the first fluid may permit the dispenser 140 to maintain and dispense the second fluid at a comparatively lower pressure. In some embodiments, the dispenser 140 may not impart any additional pressure to the second fluid, instead relying solely on gravity/hydrostatic pressure and now artificial pressurization means. Additional details regarding the dispenser 140 will be provided below.

The stem 120 may be configured to permit the flow of fluid from the base 110 vertically and expulsion of the fluid radially outward to irrigate and/or deliver a cleaning agent to a prosthetic liner positioned to surround the stem 120. As described above, the stem 120 may couple to the base through the upper aperture 119 and be positioned in fluidic communication with the duct 118. The stem 120 may comprise a fluid channel 121 extending at the lower end 122 of the stem 120 that is coupled to the base 110 to an opposing upper end 123. The coupling of the stem 120 to the base 110 may position the fluid channel 121 in fluidic communication with the duct 118. The fluid channel 121 may be defined by an interior surface of an outer wall 124 of the stem 120 or a tube positioned within a void defined by the outer wall 124.

In some embodiments, the stem 120 may comprise a plurality of holes 125 along at least a portion of the length of the outer wall 124. The plurality of holes 125 may be configured to be in fluidic communication with the fluid channel 121 such that fluid flowing through the fluid channel 121 may be expulsed through one or more of the plurality of holes 125. In some embodiments the plurality of holes 125 may be dispersed from the upper end 123 of the stem 120 downward. In some embodiments the plurality of holes 125 may be distributed along the length of the outer wall 124. The plurality of holes 125 may be distributed around the circumference of the outer wall 124.

The upper cap member 130 may be positioned in fluidic communication with the fluid channel 121 such that fluid that flows into the stem 120 via the lower end 122 may flow out of the stem 120 via the upper end 123 into the upper cap member 130. The upper cap member may comprise a sidewall 131 defining an entry aperture 132, a distributor 134, a flange 136, a first exit aperture 138, and a second exit aperture 139.

The entry aperture 132 may be configured to permit an upper portion of the stem 120 to be positioned there within and removably attached to, thereby removably attaching the upper cap member 130 to the stem 120. Such attachment may be accomplished by any means or method as is known in the art, including, but not limited to, screw fit, interference fit, magnetic coupling, fastener coupling, and the like. The removable attachment of the stem 120 to the upper cap member 130 may permit fluid to flow from the upper end 123 into the upper cap member 130 through the entry aperture 132. The fluid may then be redirected by the distributor 134 in the directions of the first exit aperture 138 and the second exit aperture 139. Moreover, the distributor 134 may redirect the flow of fluid such that the fluid exits the first exit aperture 138 and the second exit aperture 139 in a generally uniform distribution. In some embodiments, the distributor 134 may be reconfigurable to change the ratio of fluid that is redirected in the directions of the first and second exit apertures 138, 139.

The first exit aperture 138 may be generally circular such that fluid may exit from the upper cap member 130 in a complete hemisphere surrounding the upper cap member 130 generally upwards from the first exit aperture 138. In some embodiments, fluid may exit the first exit aperture 138 in a nearly complete circle with only a few interruptions in the flow. The second exit aperture 139 may be generally annular such that fluid may exit from the upper cap member 130 in a circle extending radially outward from the upper cap member 130. In some embodiments, fluid may exit the second exit aperture 139 in a nearly complete circle with only a few interruptions in the flow. It is contemplated and included within the scope of the invention that alternative embodiments may comprise only one of the first exit aperture 138 and the second exit aperture 138.

The flange 136 may be generally annular and positioned to offset a liner positioned over the upper cap member 130 from the first and second exit apertures 138, 139, thereby improving the coverage of fluid expulsed therefrom onto an inner surface of the liner. The flange 136 may further be configured to facilitate the resting of the liner thereon.

In some embodiments, the stem 120 may have a height within a range from 10 inches to 25 inches. In some embodiments, the stem 120 may have a height within a range from 12.5 inches to 22.5 inches. In some embodiments, the stem 120 may have a height within a range from 15 inches to 20 inches. In some embodiments, the stem 120 may have a height within a range from 16 inches to 19 inches. In some embodiments, the stem 120 may have a height within a range from 17 inches to 18 inches.

In some embodiments, the stem 120 may have an out diameter within a range from 0.25 inches to 2.0 inches. In some embodiments, the stem 120 may have an out diameter within a range from 0.5 inches to 1.25 inches. In some embodiments, the stem 120 may have an out diameter within a range from 0.6 inches to 1.1 inches. In some embodiments, the stem 120 may have an out diameter within a range from 0.7 inches to 1.0 inch. In some embodiments, the stem 120 may have an out diameter within a range from 0.8 inches to 0.9 inches.

Referring now to FIG. 2, additional aspects of the dispenser 140 will be discussed. The dispenser 140 may comprise a reservoir wall 142 defining a reservoir 143, a lid 144, an upper dispensing channel 146, a lower dispensing channel 147, and a flow control member 148. The reservoir wall 142 may define the sides and bottom of the reservoir 143, with a reservoir aperture 145 located in the bottom in fluidic communication with the upper dispensing channel 146. The reservoir 143 may be operable to retain the second fluid there within and permit the second fluid to flow through the reservoir aperture 145. The second fluid may be any type of cleaning agent as is known in the art, including, but not limited to, soaps, detergents, surfactants, solvents, descaling compounds, skin-protective agents, and the like. The lid 144 may cooperate with the reservoir wall 142 to define the enclosed reservoir 143. The lower dispensing channel 147 may be positioned in fluidic communication with the duct 118 immediately downstream of the venturi tube 150.

The flow control member 148 may be positioned in fluidic communication with each of the upper dispensing channel 146 and the lower dispensing channel 147 and, when in an open orientation, establish fluidic communication between the upper and lower dispensing channels 146, 147. Accordingly, the flow control member 148 may be operable to be positioned in open and close orientations, with the open orientation permitting the flow of fluid therethrough and the closed orientation preventing the flow of fluid therethrough. It is further contemplated and included within the scope of the invention that the flow control member 148 may be operable to control the flow rate of fluid flowing therethrough. The flow control member 148 may be any structure or apparatus operable to accomplish the described flow control, including, but not limited to, valves, including ball valves, barrel valves, butterfly valves, gate valves, diaphragm valves, needle valves, plug valves, solenoid valves, and the like. When in an open orientation, the second fluid may flow from the reservoir 143 and through each of the upper dispensing channel 146, flow control member 148, and lower dispensing channel 147 into the duct 118, mixing with the first fluid flowing therethrough, immediately downstream of the venturi tube 150, such that the hydrostatic pressure exerted by the second fluid in the reservoir 143 is greater than the pressure of the first fluid in the duct 118 at the point where the lower dispensing channel 147 is in fluidic communication with the duct 118.

Figure 3:
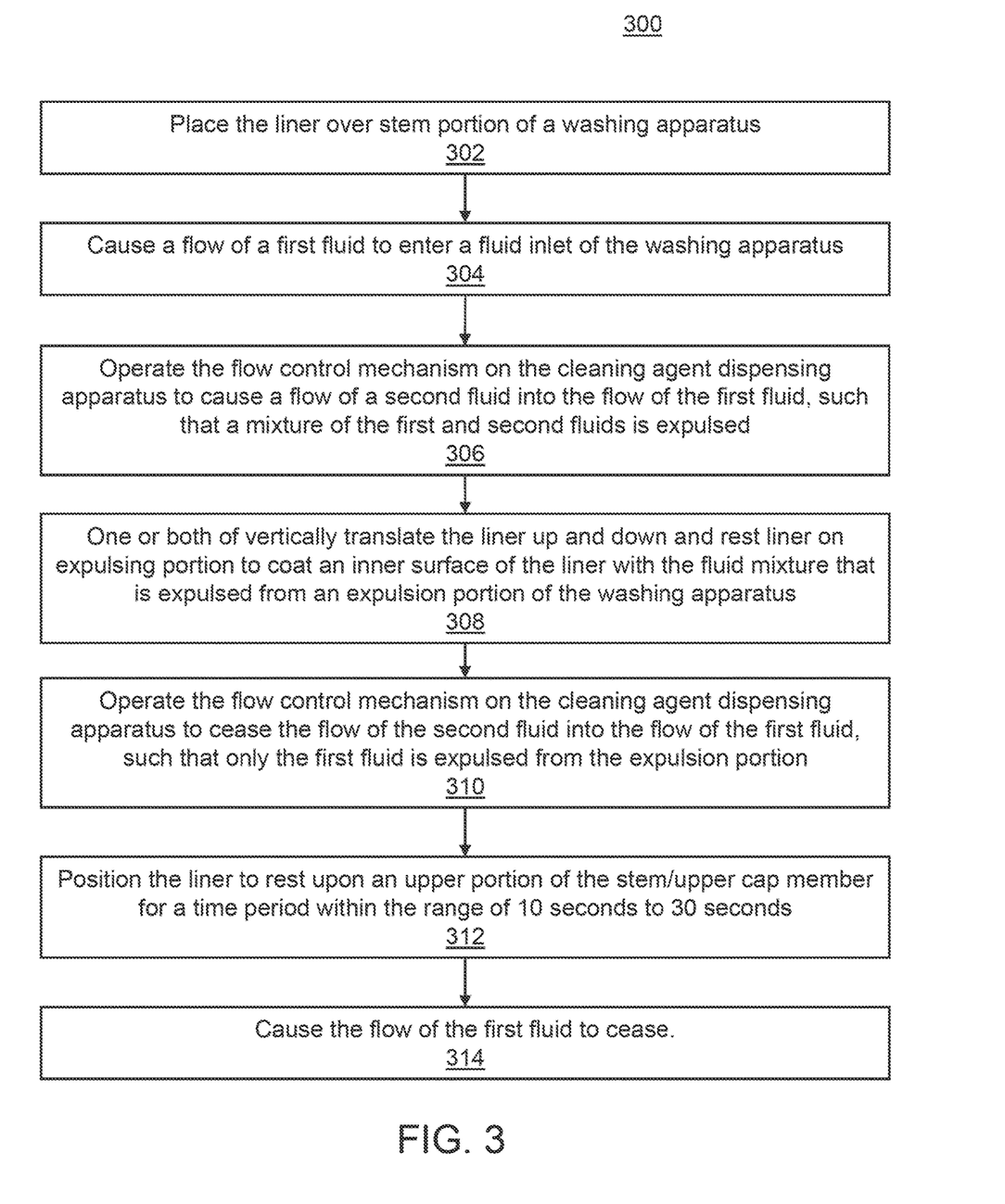
FIG. 3 is a side sectional view of the prosthetic liner cleaning apparatus of FIG. 1 with a prosthetic liner positioned over the prosthetic liner cleaning apparatus.

Referring now to FIG. 3, a method 300 of cleaning a prosthetic limb liner is presented. The method 300 may comprise placing the liner over stem portion of a washing apparatus 302. The method 300 may further comprise causing a flow of a first fluid to enter a fluid inlet of the washing apparatus 304. The method 300 may further comprise operating a flow control member, such as a valve, pump, or primer, on a cleaning agent dispensing apparatus to cause a flow of a second fluid comprising a cleaning agent to enter the flow of the first fluid within the washing apparatus, creating a fluid mixture 306. The method 300 may continue with at least one of vertically translating the liner up and down and resting the liner on the expulsion portion to coat an inner surface of the liner with the fluid mixture that is expulsed from an expulsion portion of the washing apparatus 308. The method 300 may further comprise operating the flow control mechanism on the cleaning agent dispensing apparatus to cease the flow of the second fluid into the flow of the first fluid, such that only the first fluid is expulsed from the expulsion portion 310. The method 300 may continue with positioning the liner to rest upon an upper portion of at least one of the stem and the upper cap member for a time period within the range of 10 seconds to 30 seconds 312. In some embodiments, the liner may instead be held by the user instead of resting the liner on the stem. The method 300 may conclude with causing the flow of the first fluid to cease. This method may be repeated as many times as is necessary to satisfactorily clean the liner.

Figure 4A:
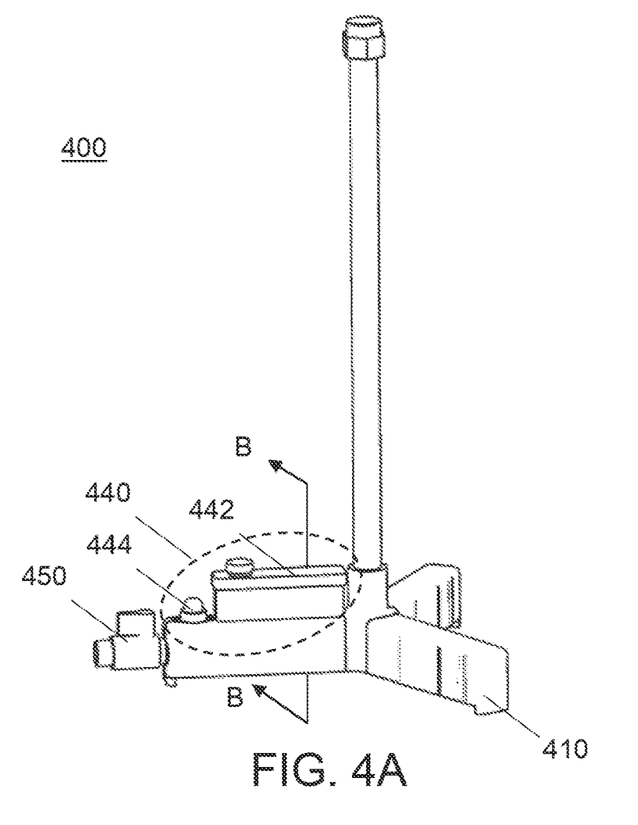
FIG. 4A is a perspective view of a prosthetic liner cleaning apparatus according to another embodiment of the invention.
Figure 4B:
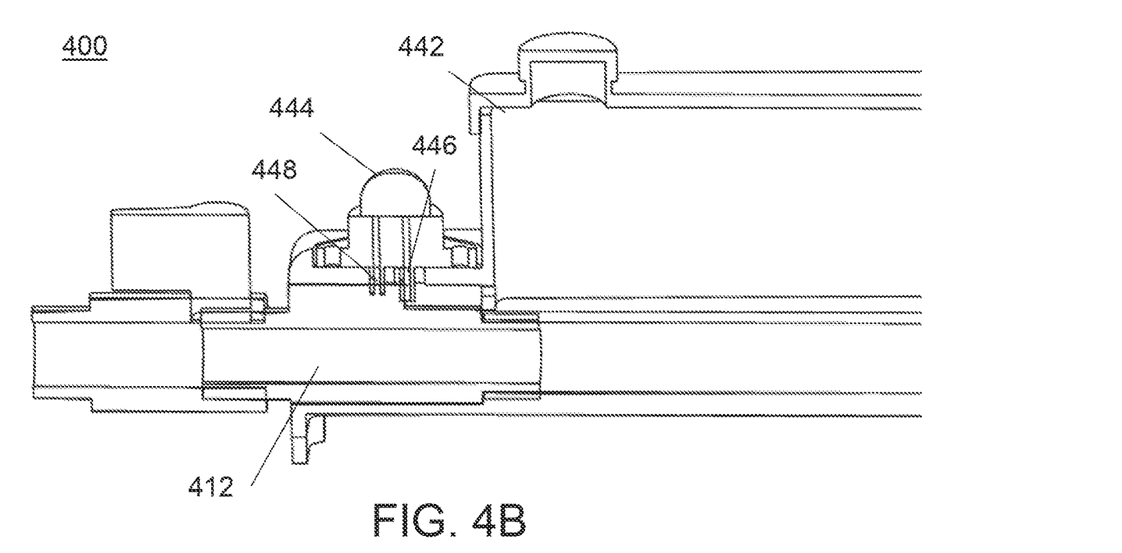
FIG. 4B is a side sectional view of a portion of the prosthetic liner cleaning apparatus of FIG. 4A taken along line B-B.

Referring now to FIGS. 4A-B, a cleaning apparatus 400 according to an embodiment of the invention is presented. The cleaning apparatus 400 may be substantially similar to the cleaning apparatus 100 of FIGS. 1-2, with a few exceptions. Specifically, the cleaning apparatus 400 may comprise a dispenser 440 comprising a reservoir 442 and a pump/primer 444. The reservoir 442 may be removably attachable to the base 410 such that, when removably attached to the base 410 it is positioned in fluidic communication with the pump 444. In other embodiments, the dispenser 440 may be at least partially integrated with the base 410. The pump 444 may be positioned in fluidic communication with an internal fluid channel 412 of the base 410 as described hereinabove. When the pump 444 is operated, it may at least one of cause fluid comprised by the reservoir to be drawn from the reservoir 442 via an inlet duct 446, through the pump 444, and into the internal fluid channel of the base 410 via an outlet duct 448 and initiate a flow of fluid from the reservoir 442, through the pump 444, and into the internal fluid channel of the base 410. The pump 444 may be any device as is known in the art operable to at least one of draw fluid from the reservoir 442 and initiate a flow of fluid from the reservoir 442 as is known in the art, including, but not limited to, bulb primers, pumps, including manual pumps, and other devices operable to create pressure differentials. In some embodiments, the pump 444 and the reservoir 442 may be independently attachable to the base 410.

Additionally, the cleaning apparatus 400 may further comprise an inlet valve 450. The inlet valve 450 may be one of positioned in communication with the base 410 and comprised by the base 410, such that the inlet valve 450 is in fluidic communication with the internal fluid channel 412 of the base 410. The inlet valve 450 may be configured to facilitate the attachment of a first fluid source thereto, such as a hose configured to expulse water into the inlet valve 450. The inlet valve 450 may be operable to be positioned in a first orientation that permits the flow of fluid therethrough and into the internal fluid channel and a second orientation that prevents the flow of fluid into the internal fluid channel 412. In some embodiments, the inlet valve may be positioned between the first and second orientations to permit the partial flow of fluid into the internal fluid channel 412. The inlet valve 450 may be any type of valve as is known in the art.

Furthermore, the cap 430 of the cleaning apparatus 400 does not comprise a flange, but may in other embodiments.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the description of the invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A prosthetic liner cleaning apparatus comprising:
    a base configured to permit a first fluid to flow therethrough, comprising:
        an input aperture;
        a center member comprising an output aperture;
        a duct in fluidic communication with each of the input aperture and the output aperture, the duct being configured to permit the first fluid to flow therethrough; and
        a plurality of legs, each leg of the plurality of legs extending outward from the center member, one leg of the plurality of legs comprising the input aperture and at least a portion of the duct, such that the duct extends from the input aperture comprised by the leg to the output aperture comprised by the center member, that same leg comprising a concavity positioned intermediate the input aperture and the duct, the concavity configured to permit tubing to be positioned there within such that the tubing passes through the input aperture, through the concavity, and be positioned in fluidic communication with the duct;
    a dispenser positioned in fluidic communication with the duct and configured to dispense a second fluid into the flow of the first fluid in the duct;
    a stem comprising a lower end, an upper end, and a fluid channel positioned in fluidic communication with each of the lower end and the upper end, the stem being attached to the base at the lower end and extending upward therefrom, and the fluid channel positioned in fluidic communication with the output aperture; and
    a cap member attached to the stem at the upper end thereof, the cap member comprising:
        an entry aperture positioned in fluidic communication with the fluid channel; and
        an exit aperture.

2. The apparatus of claim 1 wherein the duct comprises threads configured to engage with cooperating threads of the tubing to establish fluidic communication there between.

3. The apparatus of claim 1 further comprising a pressure modifying device configured to temporarily decrease the pressure of the first fluid as it flows through the base; wherein the dispenser is positioned to dispense the second fluid into the flow of the first fluid while the pressure of the first fluid is decreased.

4. The apparatus of claim 3 wherein the pressure modifying device is a venturi tube.

5. The apparatus of claim 1 wherein the dispenser comprises:
    a reservoir configured to retain the second fluid prior to being dispensed; and
    a dispensing channel positioned in fluidic communication with each of the reservoir and the duct configured to permit the second fluid to flow from the reservoir and be dispensed into the flow of the first fluid.

6. The apparatus of claim 5 wherein the dispenser further comprises a flow control member configured to control a flow rate of the second fluid through the dispensing channel.

7. The apparatus of claim 6 wherein the flow control member comprises at least one of a valve and a pump.

8. The apparatus of claim 7 wherein the dispenser is at least one of attached to and integrated with the base.

9. The apparatus of claim 5 wherein the dispenser further comprises a primer configured to at least one of draw the second fluid from the reservoir and initiate a flow of the second fluid from the reservoir.

10. The apparatus of claim 1 wherein
    the exit aperture is configured to disperse fluid into a hemispherical space generally above the cap member.

11. The apparatus of claim 1 wherein the cap member further comprises a flange extending radially outward from the cap member and configured to offset a liner placed thereupon from the cap member.

12. The apparatus of claim 1 wherein the stem further comprises a plurality of holes in fluidic communication with the fluid channel such that fluid flowing through the fluid channel is expulsed through the plurality of holes.

13. A prosthetic liner cleaning apparatus comprising:
    a base configured to permit a first fluid to flow therethrough, comprising:
        a center member comprising an output aperture;
        a plurality of legs, each leg extending radially outward from the center member;
        wherein a leg of the plurality of legs comprises:
            an input aperture;
            at least a portion of a duct; and
            a concavity positioned intermediate the input aperture and the duct, the concavity configured to permit tubing to be positioned there within such that the tubing passes through the input aperture, through the concavity, and be positioned in fluidic communication with the duct;
    a dispenser attached to the leg comprising the input aperture and positioned in fluidic communication with the duct and configured to dispense a second fluid into the flow of the first fluid in the duct, the dispenser comprising:
        a reservoir configured to retain the second fluid prior to being dispensed;

a dispensing channel positioned in fluidic communication with each of the reservoir and the duct configured to permit the second fluid to flow from the reservoir and be dispensed into the flow of the first fluid; and a pump configured to generate a flow of the second fluid from the reservoir, through the dispensing channel, and into the flow of the first fluid;

a stem comprising a lower end, an upper end, and a fluid channel positioned in fluidic communication with each of the lower end and the upper end, the stem being attached to the base at the lower end and extending upward therefrom, and the fluid channel positioned in fluidic communication with the output aperture; and a cap member attached to the stem at the upper end thereof, the cap member comprising:

an entry aperture positioned in fluidic communication with the fluid channel; and an exit aperture configured to disperse fluid into a hemispherical space generally above the cap member.

14. The apparatus of claim 13 further comprising a pressure modifying device configured to temporarily decrease the pressure of the first fluid as it flows through the base; wherein the dispenser is positioned to dispense the second fluid into the flow of the first fluid while the pressure of the first fluid is decreased.

15. The apparatus of claim 13 wherein the cap member further comprises a flange extending radially outward from the cap member and configured to offset a liner placed thereupon from the cap member.

* * * * *